United States Patent [19]

Harms et al.

[11] Patent Number: 4,820,305
[45] Date of Patent: Apr. 11, 1989

[54] PLACE HOLDER, IN PARTICULAR FOR A VERTEBRA BODY

[76] Inventors: Jürgen Harms, Am Rüppurrer schloss, 7500 Karlsruhe; Lutz Biedermann, Am Schäfersteig 8, 7730 VS-Villingen, both of Fed. Rep. of Germany

[21] Appl. No.: 115,178

[22] Filed: Oct. 30, 1987

[30] Foreign Application Priority Data

Nov. 3, 1986 [DE] Fed. Rep. of Germany ....... 3637314

[51] Int. Cl.⁴ ............................ A61F 2/28; A61F 2/44
[52] U.S. Cl. ........................................ 623/16; 623/17; 128/92 YM; 128/92 YJ; 128/92 YF
[58] Field of Search ............ 623/16, 17, 11, 12, 623/66; 128/92 Y, 92 YZ, 92 M, 92 YJ, 92 YF, 92 YD, 92 R, 343

[56] References Cited

U.S. PATENT DOCUMENTS

| | | | |
|---|---|---|---|
| 3,426,364 | 2/1969 | Lumb | 128/92 YM X |
| 3,710,789 | 1/1973 | Ersek | 128/92 YZ |
| 3,867,728 | 2/1975 | Stubstad et al. | 623/17 |
| 3,875,595 | 4/1975 | Froning | 623/17 |
| 4,309,777 | 1/1982 | Patil | 623/17 |
| 4,501,269 | 2/1985 | Bagby | 128/92 YJ |
| 4,522,200 | 6/1985 | Stednitz | 128/92 YZ |
| 4,657,550 | 4/1987 | Daher | 623/17 |
| 4,733,665 | 3/1988 | Palmax | 128/343 |
| 4,739,762 | 4/1988 | Palmaz | 128/343 |

FOREIGN PATENT DOCUMENTS

| | | |
|---|---|---|
| 2340546 | 2/1975 | Fed. Rep. of Germany ........ 623/17 |
| 3023942 | 6/1980 | Fed. Rep. of Germany . |
| 3435771 | 9/1984 | Fed. Rep. of Germany . |
| 0973117 | 11/1982 | U.S.S.R. .............................. 623/17 |

OTHER PUBLICATIONS

Post—Sintering Heat Treatments for Porous Coated Ti—GAl—4V Alloy, Steven Cook et al., 1985, Marcel Dekker Inc., pp. 37-50.

Primary Examiner—Richard J. Apley
Assistant Examiner—David J. Bender
Attorney, Agent, or Firm—R. T. Gammons

[57] ABSTRACT

A prosthesis in the form of a hollow, cylindrical jacket for insertion in the gap between adjacent bone ends, the jacket being provided with reticulated sides and with toothed ends for engagement with the bone ends.

10 Claims, 3 Drawing Sheets

PLACE HOLDER, IN PARTICULAR FOR A VERTEBRA BODY

BACKGROUND OF THE INVENTION

The invention is for a prosthesis comprising a place holder or dummy element in particular for a prosthesis comprising a vertebra body.

Whenever a vertebra/body has to be removed from the spinal column or a bone piece from a bone, it is necessary to insert a place holder or dummy element between the remaining parts of the spinal column or the bone, respectively.

There is known from the ends of the bone German patent specification No. 30 23 942 a place holder, called implant, as vertebra body substitute for insertion between vertebrae/body of the spinal column. The two opposed supporting ends of the place holder are dish-shaped and comprise cylindrical projections. The adjacent vertebrae/body are formed such that the connection of the supporting ends with the adjacent vertebrae/body is possible.

There is known from the German laid open print No. 34 35 771 a bone matrix which comprises a plurality of holes for improving the stimulation of bone formation and of the bone regeneration. As a function of the piece to be substituted, the matrix is plate-shaped, semi-cylindrical or cylindrical. If such a bone matrix were placed between two vertebrae/body, a separate connection to the adjacent vertebrae/body would have to be provided.

OBJECTS OF THE INVENTION

It is an object of the invention to provide an improved place holder. It is a further object to design a place holder such that it can easily be inserted between two adjacent vertebrae/body or two adjacent bone pieces.

SUMMARY OF THE INVENTION

In order to achieve the above mentioned objects the invention provides a place holder, in particular for a vertebra/body, comprising a jacket-shaped member having at least one aperture in the wall thereof and an upper edge and a lower edge, both edges being at least partly serrated. It is thus achieved that a rotation-secured connection may be provided between the pieces to be connected. If desired, material to be introduced into the interior may be entered through the aperture. The aperture may eventually also serve for receiving a pedicle screw.

Further embodiments of the invention are characterized in the dependent claims.

BRIEF DESCRIPTION OF THE DRAWINGS

Further advantages, features and objects of the invention will stand out from the following description of exemplary embodiments with reference to the drawings, wherein.

DESCRIPTION OF THE PREFERRED EMBODIMENTS

Figure 1:
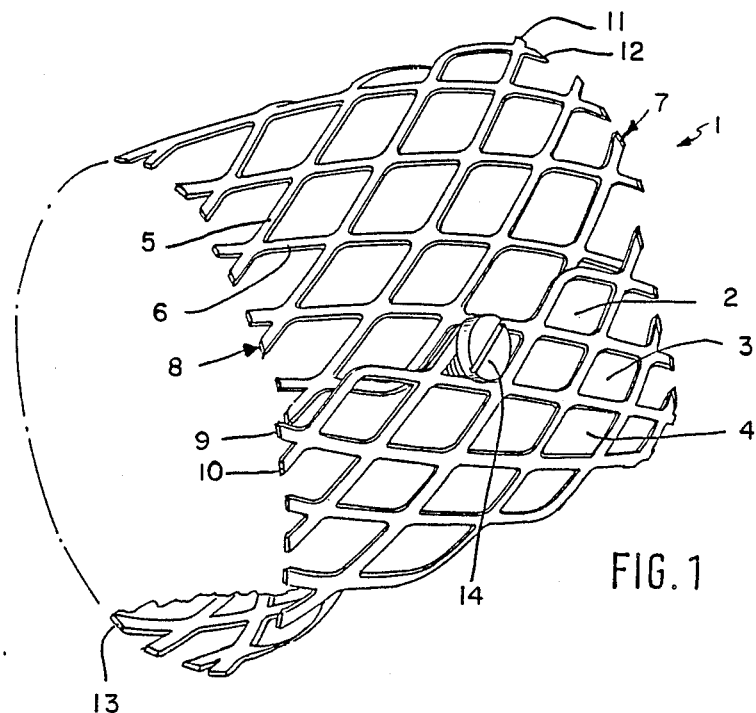
FIG. 1 is a perspective view of an embodiment of the invention.

As may in particular be seen from FIG. 1, a prosthesis comprising a place holder or dummy element 1 is formed as a cylinder jacket-shaped member. In the manner shown in FIG. 1, the cylinder jacket comprises rhombus-shaped apertures 2 having their longitudinal diagonal extending parallel to the cylinder axis. Respective adjacent rows 3, 4 of such rhombuses are mutually offset by half of the rhombus height. In this manner a grid of band strips 5, 6 is formed which intersect each other with an acute angle and which are inclined by respective identical angles with respect to the longitudinal diagonal of the rhombuses. It is thus achieved that a load acting onto the place holder in the direction of its longitudinal axis is taken up in uniform manner.

Figure 2:
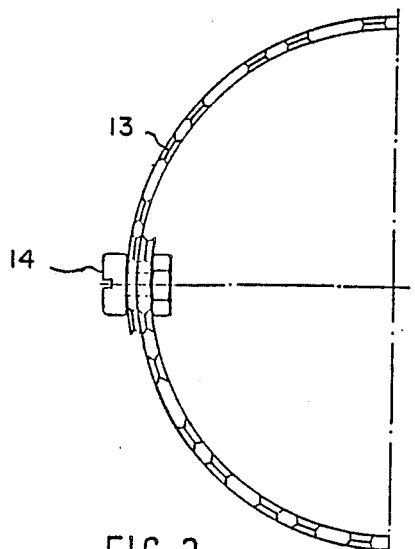
FIG. 2 is a top view of the apparatus of FIG. 1 in partial representation.

The upper edge 7 and the lower edge 8 are each formed such that approximately V-shaped teeth 9, 10 or 11, 12, respectively project upwards and downwards in the plane of the jacket parallel to the cylinder axis. The ends 13 of the teeth are bezelled or chamfered such that both chamfered faces intersect with an angle of approximately 45° such that a type of cutting edge is formed. In the embodiment shown in the FIGS. 1 and 2 the jacket is formed by rolling up a correspondingly designed/sheet material and especially sheet metal strip. The two overlapping ends are interconnected by means of a screw 14.

Figure 3:
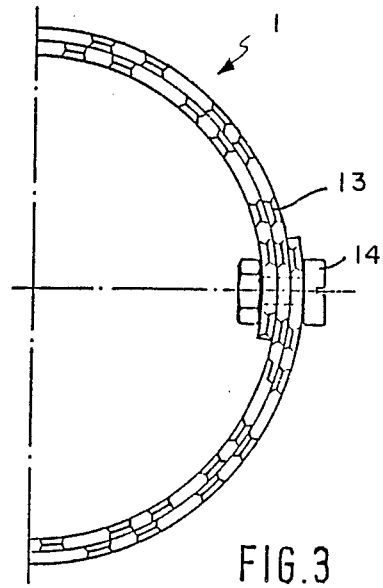
FIG. 3 shows a modified embodiment in a representation corresponding to that of FIG. 2.

It is generally possible to reinforce the wall of the jacket by using two windings in the manner shown in FIG. 3.

In operation the place holder is inserted in axial direction between the remaining vertebrae/body or bone pieces in place of a removed vertebra/body or bone piece. The diameter and the axial length of the jacket are selected such that the jacket fits between the remaining pieces in that manner that these pieces keep their original distance from each other. The teeth 9, 10 and 11, 12, respectively, of the place holder engage the surface of the adjacent vertebrae/body or bones, respectively, in that manner that a torsional movement of the one adjacent part with respect to the other adjacent part is transferred to the respective other adjacent part or braked or reduced, respectively, by means of the projecting teeth. At least the interior of the jacket is filled with bone cement through the apertures. If desired, that much bone cement may be introduced that the cement penetrates outwardly through the apertures and a molding at the outside is performed. Preferably the bone cement is filled in after insertion of the above described jacket. However, it is also possible to fill the interior space of the jacket before insertion thereof.

Figure 4:
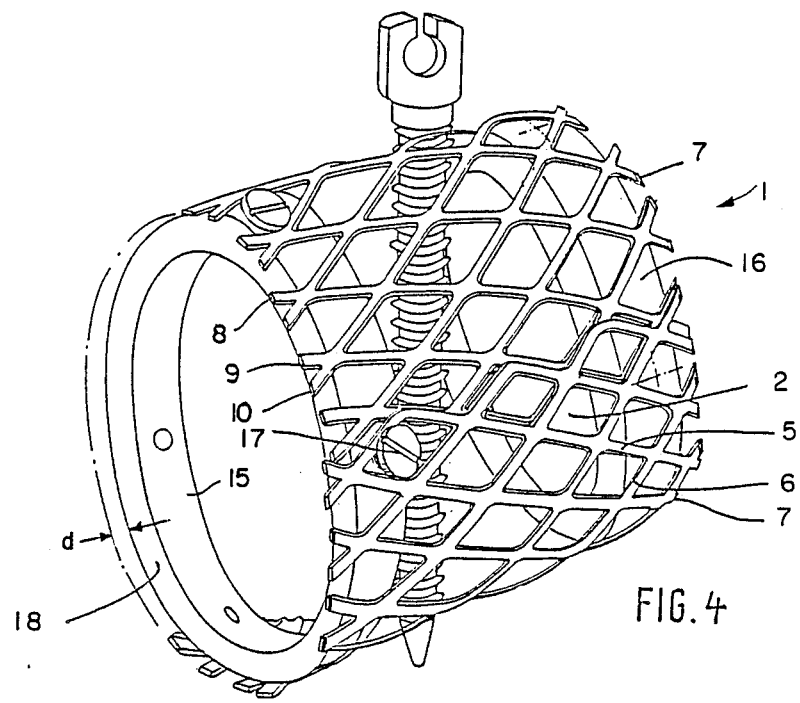
FIG. 4 shows a modified embodiment in a representation corresponding to that of FIG. 1.
Figure 5:
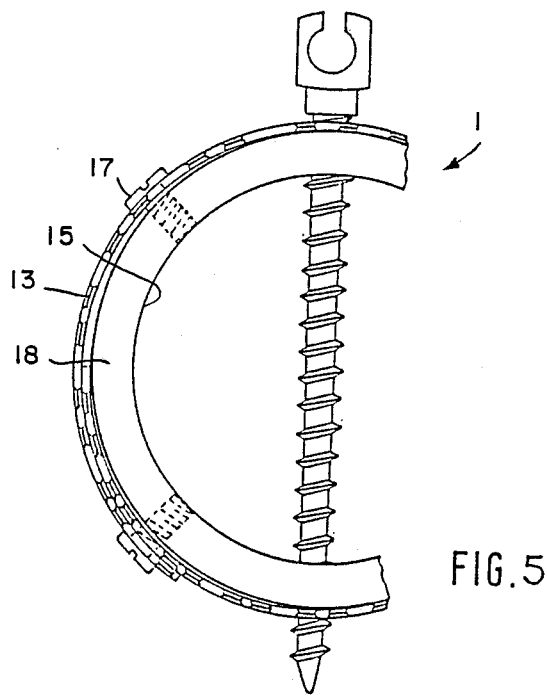
FIG. 5 is the modified embodiment in a representation corresponding to that of FIG. 2.

In the modified embodiments shown in the FIGS. 4 and 5 corresponding parts are referred to by the respective identical reference sign. This embodiment differs from the above described in that cylindrical rings 15, 16 having an outer diameter which conforms to the respective inner diameter of the cylindrical jacket-shaped member are provided at the two opposed ends of the cylindrical body. The cylinder jacket is rigidly connected with the close lying ring 15, 16 by means of respective screws 17. The outwardly directed side 18 of the respective ring 15, 16 has a distance d from the adjacent edge 7 or 8, respectively. This distance is preferably in the order of 0.5 to 2 mm. In inserting the jacket the ends projecting beyond the respective ring are pressed into the adjacent bone when subjected to load. The adjacent ring prevents a further penetration into the adjacent bone. The desired value of the distance d is determined by the intended way of use and the depth of penetration desired therefor.

As may be seen from the FIG. 4 and 5, the dimensions of the rhombus-shaped apertures are selected such that the thread of a pedicle screw may be screwed into the aperture. Thus, an additional simple fixation between the place holder and the respective adjacent vertebrae/body or bone pieces may be achieved.

Figure 6:
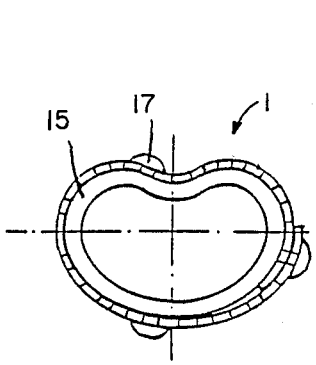
FIG. 6 is a bottom view of a modified embodiment.
Figure 7:
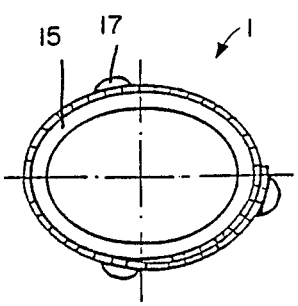
FIG. 7 is a bottom view of a further embodiment.

In the above described embodiments the cross-section is circular. Preferably the cross-section is chosen as a function of the cross-section of the parts to be connected. For connection of vertebrae/body in the lumbal region the member preferably comprises a kidney-shaped cross-section shown in FIG. 6 or an oval cross-section shown in FIG. 7.

Figure 8:
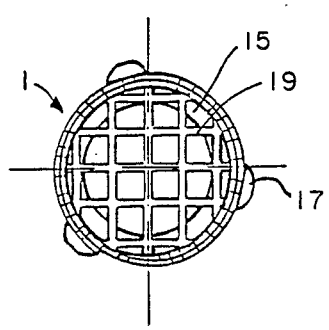
FIG. 8 is a bottom view of an embodiment as shown in FIGS. 4 and 5, but including a bottom plate.
Figure 9:
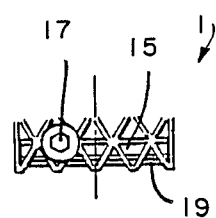
FIG. 9 is a lateral view of the lower section of the embodiment shown in FIG. 8.

The embodiment shown in the FIGS. 8 and 9 additionally comprises a bottom plate 19 at the bottom side and a corresponding top plate at the opposite side. The bottom plate and the top plate are each grid-shaped. The adjacent rings 15 and 16, respectively, serve as abutments. This embodiment is particularly suitable for the connection of porous bones. By means of the bottom plate and top plate, respectively, it is prevented that the place holder sinks too far into e.g. the vertebrae/body cover plate. The bottom plate and top plate, respectively, preferably comprise a grid-shaped structure shown as an example in FIG. 8.

As mentioned above, the interior may be filled with bone cement. In place of the filling with bone cement, however, it is also possible to insert a piece of bone from the patient or from another source into the interior of the place holder such that the place holder has a supporting function around the inserted bone piece. Both when filling with bone cement and when inserting the bone piece a particularly secure connection with the above described place holder is achieved. In addition, a safe protection of the spinal cord channel against ejected bone cement or bone pieces is achieved.

While the invention has been described in preferred form it is not limited to the precise nature shown as various modifications may be made without departing from the scope of the appended claims.

What is claimed is:

1. A prosthesis for insertion in a gap between vertebra wherein a damaged vertebra body has been removed and/or for insertion in a gap between parts of a bone from which a damaged part has been removed, comprising a generally cylindrical jacket disposed in the gap to be secured at its opposite ends to the opposite ends of the vertebra at opposite ends of the gap and/or the opposed ends of the parts of the bone at opposite ends of the gap, said cylindrical jacket comprising a metal tubular structure of a cross section corresponding to substantially the cross section of the opposed ends to be connected, said tubular structure containing a plurality of apertures disposed circumferentially and longitudinally thereof and wherein there are teeth at the opposite ends of the tubular structure, adjacent teeth extending peripherally in opposite directions and wherein the tubular structure is formed of sheet material formed into a cylinder with its ends overlapping and secured to each other by one or more screws engaged within apertures in the overlapping ends and wherein the teeth are bezelled such that the bezelled ends define acute angles forming cutting edges.

2. A prosthesis according to claim 1 wherein the jacket is formed of two layers of sheet metal disposed in concentric relation with each other and secured by said screws.

3. A prosthesis according to claim 1 wherein the jacket is of a length such that it fits between the adjacent bone ends with the teeth engaged with the surface of the adjacent bones to thus hold the bone ends at the original distance from each other.

4. A prosthesis according to claim 1 wherein the gap between the bone ends enveloped by the jacket is filled with bone cement.

5. A prosthesis according to claim 1 wherein there are annular rings of a diameter corresponding to the interior diameter of the jacket disposed within the jacket adjacent to but spaced from the ends and screws securing the rings in place, wherein the rings limit penetration of the teeth ends into the bone ends.

6. A prosthesis according to claim 5 wherein the distance between the ends of the jacket and the rings is in the order of 0.5 to 2 millimeters.

7. A prosthesis according to claim 1 wherein the jacket is of oval cross section.

8. A prosthesis according to claim 1 wherein the cross section of the jacket is kidney-shaped.

9. A prosthesis according to claim 1 wherein there are plates disposed within the jacket at the opposite ends thereof and diametrically thereof at a predetermined distance from the ends.

10. A prosthesis according to claim 9 wherein the plates are grid-shaped.

* * * * *